United States Patent
Johnson et al.

(10) Patent No.: US 6,719,717 B1
(45) Date of Patent: Apr. 13, 2004

(54) THROMBECTOMY TREATMENT SYSTEM AND METHOD

(75) Inventors: Matthew S. Johnson, Carmel, IN (US); Stephen G. Lalka, Carmel, IN (US)

(73) Assignee: Advanced Research & Technology Institute, Inc., Indianapolis, IN (US)

(*) Notice: Subject to any disclaimer, the term of this patent is extended or adjusted under 35 U.S.C. 154(b) by 0 days.

(21) Appl. No.: 09/527,155

(22) Filed: Mar. 17, 2000

(51) Int. Cl.⁷ .......................... A61M 37/00; A61M 1/00
(52) U.S. Cl. .................. 604/9; 604/5; 604/6.09; 604/6.11; 604/35
(58) Field of Search .................. 604/4.01, 5.01, 604/6.09, 6.16, 27, 35, 19–20, 104–107, 319, 323, 8–10

(56) References Cited

U.S. PATENT DOCUMENTS

| | | | |
|---|---|---|---|
| 3,946,731 A | | 3/1976 | Lichtenstein |
| 4,817,600 A | | 4/1989 | Herms et al. |
| 4,832,055 A | | 5/1989 | Palestrant |
| 4,957,501 A | | 9/1990 | Lahille et al. |
| 5,234,403 A | * | 8/1993 | Yoda et al. .................. 210/650 |
| 5,279,546 A | | 1/1994 | Mische et al. |
| 5,329,942 A | | 7/1994 | Gunther et al. |
| 5,368,034 A | | 11/1994 | Isner |
| 5,370,657 A | | 12/1994 | Irie |
| 5,380,299 A | | 1/1995 | Fearnot et al. |
| 5,419,774 A | * | 5/1995 | Willard et al. .................. 604/22 |
| 5,458,574 A | * | 10/1995 | Machold et al. ....... 604/101.03 |
| 5,531,788 A | | 7/1996 | Dibie et al. |
| 5,536,412 A | | 7/1996 | Ash |
| 5,554,117 A | | 9/1996 | Ensminger et al. |
| 5,562,698 A | | 10/1996 | Parker |
| 5,601,595 A | | 2/1997 | Smith |
| 5,607,579 A | * | 3/1997 | Latham et al. .................. 210/109 |
| 5,626,605 A | | 5/1997 | Irie et al. |
| 5,681,347 A | | 10/1997 | Cathcart et al. |
| 5,702,368 A | * | 12/1997 | Stevens et al. .................. 604/171 |
| 5,713,849 A | * | 2/1998 | Bosma et al. .................. 604/28 |
| 5,725,552 A | | 3/1998 | Kotula et al. |
| 5,746,767 A | | 5/1998 | Smith |
| 5,800,457 A | | 9/1998 | Gelbfish |
| 5,827,229 A | * | 10/1998 | Auth et al. .................. 604/164.13 |
| 5,858,238 A | | 1/1999 | McRea et al. |
| 5,925,063 A | | 7/1999 | Khosravi |
| 5,938,645 A | * | 8/1999 | Gordon .................. 604/171 |
| 6,010,531 A | * | 1/2000 | Donlon et al. .................. 623/2.1 |
| 6,059,745 A | * | 5/2000 | Gelbfish .................. 604/6.09 |
| 6,120,474 A | | 9/2000 | Okuda et al. |
| 6,146,396 A | * | 11/2000 | Konya et al. .................. 606/159 |

OTHER PUBLICATIONS

Evans, Michael. Method and system for re–infusing filtered bodily aspirates. PGPubs Dec. 6, 2001, Filed Dec. 31, 1999. PGPub U.S. 2001/0049486.*

(List continued on next page.)

*Primary Examiner*—Angela D. Sykes
*Assistant Examiner*—Leslie R. Deak
(74) *Attorney, Agent, or Firm*—Donald R. Piper, Jr.; Dann, Dorfman, Herrell & Skillman

(57) ABSTRACT

A thrombectomy treatment system and method are provided. The system includes a catheter for insertion into the vascular system of a patient so that a tip of the catheter is positioned in the vicinity of a blood clot to be removed from the patient. A suction source is provided to withdraw the blood clot from the patient through the catheter. A filtration device functions to remove the blood clot from the accompanying blood. The filtered blood is collected in a blood collection device. A blood reinfuser communicates with the blood collection device to reinfuse the filtered blood back into the patient.

6 Claims, 3 Drawing Sheets

OTHER PUBLICATIONS

Muller=Hulsbeck, et al. "Vacuum Pump Controlled Aspiration Thrombectomy: In Vitro Comparison with a Thrombus Fragmentation Procedure" Fortschr. Rontgenstr., vol. 168 (1998), No. 2, pp. 191–194 (English translation attached).

Thrmel–Rodrigues et al. "Manual Thromboaspiration and Dilation of Thromosed Dialysis Access: Mid–Term Results of a Simple Concept" J. Vasc. Interv. Radiol 1997 Sep–ct; 8 (5) :813–24.

Brossmann, et al. "Percutaneous Balloon–Assisted Thrombectomy: Preliminary In Vivo Results with an Expandable Vascular Sheath System" Radiology 1998; 206;439–445.

Guy S. Reeder, MD et al., "Apiration Thrombectomy for Removal of Coronary Thrombus," The American Journal of Cardiology, p. 107–110, (Jul. 1, 1992).

F. Poulain et al., "Local Thrombolysis and Thromboaspiration in the Treatment of Acutely Thrombosed Arteriovenous Hemodialysis Fistulas," Cardiovascular Intervent Radiology, Spinger–Verlag New York Inc., p. 98–101, (1991).

Hans–Joachim Wagner et al., "Long–Term Results of Percutaneous Aspiration Embolectomy," Cardio Vascular and International Radiology, Springer–Verlag New York Inc., vol. 17, p. 241–246, (1994).

Erhard E. Starck, MD et al., "Percutaneous Aspiration Thromboembolectomy," Radiology, p. 61–66, (Jul., 1985).

Rolf W. Guenther, MD et al., "Aspiration Catheter for Percutaneous Thrombectomy: Clinical Results[1]," Radiology, vol. 175 (No. 1) p. 271–273, (1990).

Melhem J. A. Sharafuddin, MD et al., "Percutaneous Balloon–assisted Aspiration Thrombectomy of Clotted Hemodialysis Access Grafts[1]," Journal of Vascular and International Radiology, vol. 7 (No. 1), p. 177–183, (1996).

Tatsuaki Murakami, MD et al., "Intracoronary Aspiration Thrombectomy for Acute Myocardial Infarction," The American Journal of Cardiology, Excerpia Medica, Inc., vol. 82, p. 839–844 (Oct. 1, 1998).

Jacob Shani, MD et al., "Mechanical Manipulation of Thrombus: Coronary Thrombectomy, Intracoronary Clot Displacement, and Transcatheter Aspiration," The American Journal of Cardiology, vol. 72, p. 116G–118G, (Dec. 16, 1993).

Mark Dooris, MBBS et al., "Successful Reversal of Cardiogenic Shock Precipitated by Saphenous Vein Graft Distal Embolization Using Aspiration Thrombectomy," Catherization and Cardiovascular Diagnosis, Wiley–Liss, Inc., vol. 33, p. 267–271, (1994).

S. Mitchell Rivitz et al., Percutaneous Aspiration Thrombectomy of an Acutely Occluded Aortoernal Bypass Graft, Interventional Radiology Case Conference Massachusetts General Hospital, American Journal of Radiology, p. 455–458, (1995).

Letters to Editor regarding article entitled, "Percutaneous Aspiration Thromboembolectomy", written by Klaus Rauber, MD.

* cited by examiner

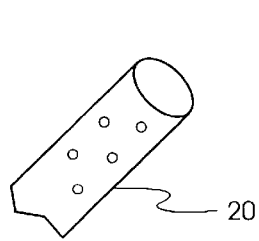
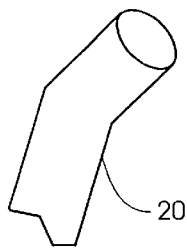
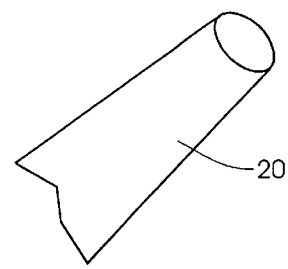
FIG. 2A  FIG. 2B  FIG. 2C
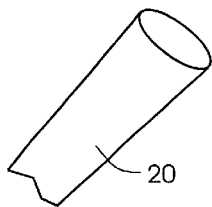
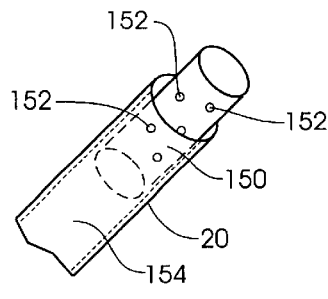
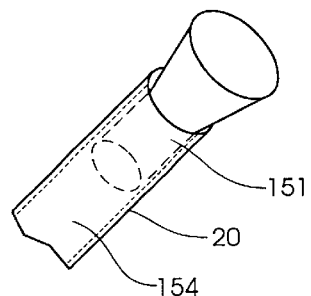
FIG. 2D  FIG. 2E  FIG. 2F
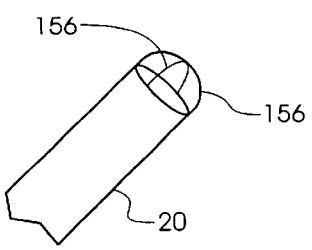
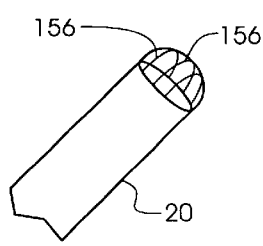
FIG. 2G  FIG. 2H

THROMBECTOMY TREATMENT SYSTEM AND METHOD

FIELD OF THE INVENTION

The present invention relates generally to a thrombectomy treatment system and method, and more particularly to a percutaneous thrombectomy system and method providing reinfusion of treated blood that is free of blood clots.

BACKGROUND OF THE INVENTION

Blood clots, such as emboli and thrombi, can pose serious health risks, making treatment and removal of the clots highly desirable. Blood clots may form on the interior surface of a blood vessel and grow in size to occlude the blood vessel at the point of clot formation. Alternately, a portion of the clot may break free forming an embolus capable of occluding a blood vessel anywhere within the vascular system.

When the obstruction occludes a vessel supplying blood to the brain, a stroke may result causing temporary or lasting paralysis of a part of the body or, in severe cases, death. Obstruction of the pulmonary artery or one of its branches can create difficulty in breathing and can potentially cause the patient to die. Blockage of other blood vessels can occur as well causing attendant health concerns. Given the potentially irreversible and destructive nature of such blockage, safe and effective procedures are needed to eliminate clots from the vascular system.

Many factors can contribute to the likelihood of clot formation, including injury to a blood vessel, alterations from normal blood flow, changes in the coagulability of the blood, and formation of fatty plaques on the lining of a blood vessel (atherosclerosis). An abrupt, abnormal change in diameter of a blood vessel wall, such as an aneurysm, increases the potential for blood coagulation. Other factors such as confinement in bed may also result in more sluggish blood flow in the veins and consequent formation of a clot.

Dialysis grafts can disrupt blood flow to an extent that increases the risk of clot formation within the vicinity of the graft junction. Additionally, surface character and compliance mismatch of some graft materials may cause turbulence in the blood flow, which in turn may lead to hemolysis of red cells, provide sites for mural bacterial adhesion and subsequent colonization, and, in areas of blood stasis, promote thrombosis and blood coagulation. Accordingly, dialysis patients are at increased risk for the formation of blood clots in the vicinity of the dialysis graft.

The present invention addresses these concerns by providing a system and a method for removing clots from the vascular system of a patient by withdrawing blood and clots from the patient, filtering the blood to remove the clots, and reinfusing the filtered blood back into the patient.

SUMMARY OF THE INVENTION

An apparatus for removal of blood clots from the blood vessel system of a patient is provided whereby clots such as thrombi and/or emboli are extracted from the patient with some of the patient's blood. As used herein "blood vessel system" includes grafts as well as naturally occurring blood vessels. The blood containing emboli or thrombi is then filtered in a filter unit and collected in a blood collection container. A blood reinfuser communicates with the blood collection container to enable the filtered blood to be reinfused back into the patient. As a result, the reinfusion of filtered blood that is free from blood clots is safely effected.

More specifically, the system comprises a percutaneous catheter assembly, a blood filtration device, a suctioning source, and a reinfuser. The catheter assembly comprises a main catheter for insertion into a selected blood vessel of a patient to permit blood and blood clots to be removed from the patient. The catheter end is positioned at a selected target site to effect removal of a blood clot. The catheter assembly may include a port through which a guidewire, a declotting device such as a thrombolytic device or a balloon, may be inserted to assist in the dislodgement and removal of the blood clot. The end of the catheter may comprise one of various differently configured tips suited to the removal of blood clots. In a selected arrangement, the catheter assembly is in fluid communication with a Y-junction adapter which has one branch in fluid communication with the filtering device to permit the blood to be filtered and a second branch in fluid communication with a waste container to permit disposal of the removed clots.

The main catheter is in fluid communication with a blood filtration device. The filtration device comprises a filter suitable for separating blood clots from the blood and a blood collection device for collecting the filtered blood. The filtration device is in communication with a suctioning source, such as a motorized pump, which provides suction to the main catheter through the filtration device. Application of suction causes blood clots and any accompanying blood from the patient to be withdrawn from the target site through the main catheter and into the filtration device, where the accompanying blood is separated from the blood clots. A reinfuser is in fluid communication with the blood collection device and comprises a delivery device, such as an intravenous (IV) needle and tubing, to reinfuse the filtered blood back into the patient.

In one arrangement, the blood collection device may be separated from the filtration device and attached to the reinfuser for reinfusion of the filtered blood into the patient. In an alternate arrangement, the reinfuser may function to reinfuse the filtered blood to the patient while the blood collection device remains attached to the filtration device.

By the method of the present invention, a catheter is inserted into a graft or a selected blood vessel of a patient and is advanced until the distal end of the catheter is located at a selected target site at a blood clot. Suction is applied to a blood filtration device which is in fluid communication with the proximal end of the catheter. The suction draws the blood clot and any accompanying blood into the distal end of the catheter removing the clot from the patient. The removed blood and blood clot are transported through the catheter into the filtration device where the blood is filtered to separate the clot from the blood. The collected, filtered blood is then reinfused back into the patient through the reinfuser. The filtered blood may be reinfused into the patient while the catheter remains in place. Alternatively, the reinfusion may be effected subsequent to the suctioning to remove the blood clot. Optionally, the reinfusion may be effected through the catheter.

In a selected mode of operation of the current invention, a device, such as a thrombolytic device, is inserted into the catheter and is used to break up the blood clot at the distal end of the catheter prior to removal of the blood clot fragments by suction through the catheter. Optionally, a thrombolytic agent may be introduced through the catheter or systemically to aid in dissolution of the clot prior to removal. In applications where it is not desirable to filter the suctioned clot, the suctioned blood, or a portion of the suctioned blood, may be diverted into a waste container.

BRIEF DESCRIPTION OF THE DRAWINGS

The foregoing summary and the following detailed description of the preferred embodiments of the present invention will be best understood when read in conjunction with the appended drawings, in which:

FIGS. 2 A–H are schematic perspective views of alternate catheter tips for use in treating blood clots in accordance with the present invention.

DETAILED DESCRIPTION OF THE INVENTION

Figure 1:
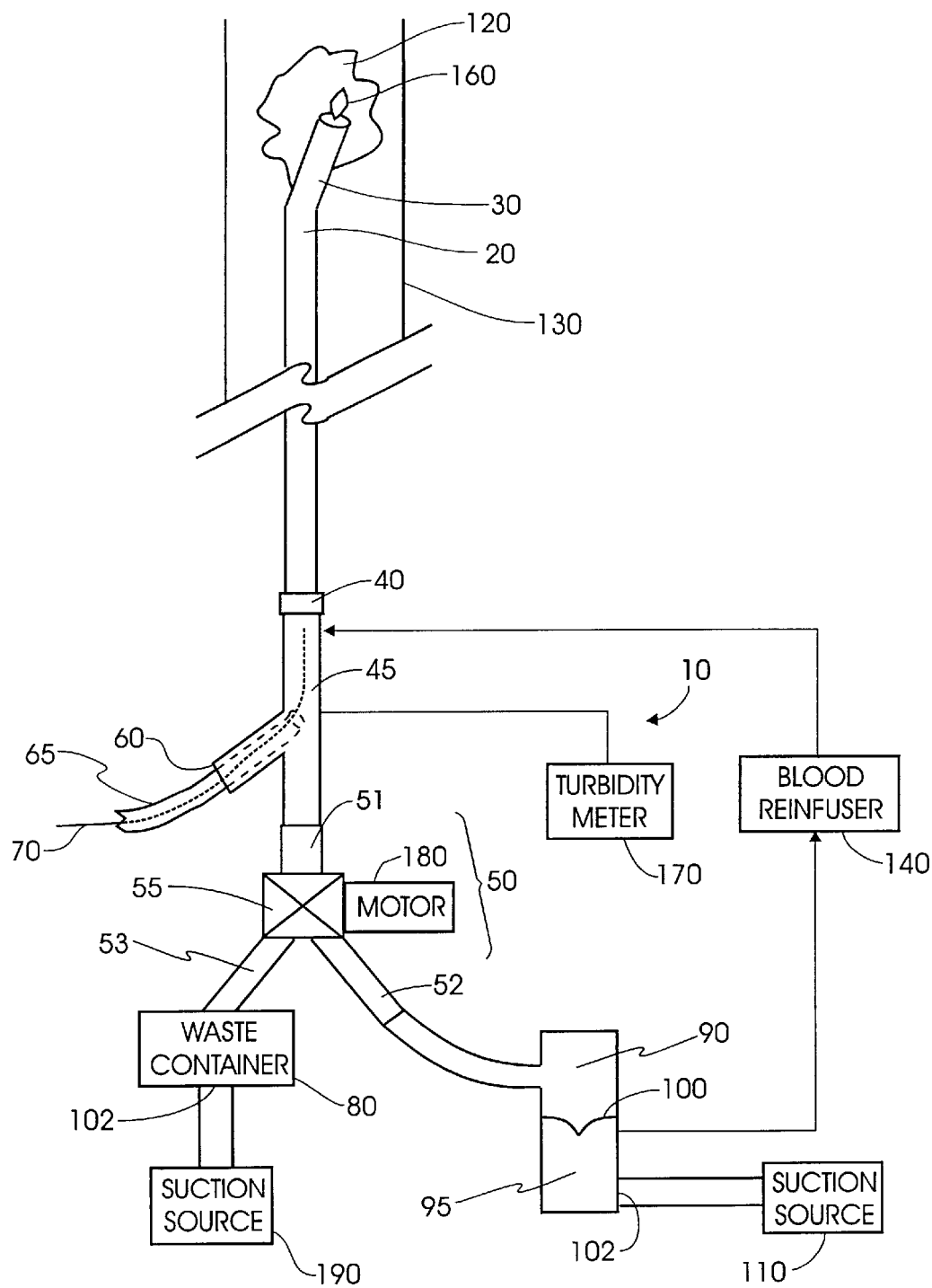
FIG. 1 is a schematic view, partially in section, showing the system of the present invention for treating blood clots.

Referring now to the drawings, a percutaneous thrombectomy treatment system 10 is provided for enabling the removal of blood clots from a patient's body. The blood clot is removed from the patient's body by dislodging the clot and suctioning the clot with any accompanying blood from the patient's body. The suctioned blood and clot are then filtered external to the body to extract the clots from the filtered blood. Reinfusion of the filtered blood back into the patient's body is then effected.

The treatment system 10 comprises a first flexible, longitudinally elongated tubular member, such as a catheter 20, suitable for insertion into the vascular system of a patient for the withdrawal of blood clots 120 and accompanying blood. Catheter 20 is formed of a suitable pliable material and includes a distal tip 30 for insertion into a selected lumen of the patient and a proximal end for connection with a source of suction 110.

The proximal end of catheter 20 is in fluid communication with a blood filtration device 90 so that the blood clot and the accompanying blood is drawn through the catheter and into the filtration device 90 by the source of suction 110. The filtration device 90 comprises a filter 100 suitable for capturing and separating blood clots 120 from the withdrawn blood. The filtration device 90 is in fluid communication with a blood collection device 95 for collecting the filtered blood. The filtration device 90 is further in gaseous communication with a suction source 110 which provides suction to the catheter 20 through the filtration device 90. Application of suction withdraws blood clots 120 and any accompanying blood from the patient through the catheter 20 into the filtration device 90, where the accompanying blood is separated from blood clots 120 by filter 100. A valve or safety seal 102 may be utilized to prevent the flow of the filtered blood from blood collection device 95 into suction source 110. The source of suction is preferably connected with the blood collection device 95 at a position vertically higher than the highest level of collected blood to prevent any blood flow into the source of suction 110. The blood may be drawn through filter 100 by the force of gravity, the force of suction, by centrifugal force or by any combination of such forces. When centrifugal force is used, a centrifuge unit may be incorporated in or connected with the filtration device 90.

The proximal end of catheter 20 is operably connected to filtration device 90 via an adapter 45 and rotating hub connector 40. The hub 40 is rotatably mounted on the adapter and functions to rotatably connect the catheter with the adapter in a fluidly sealed manner. The adaptor 45 includes a side branch 60 through which a guidewire 70 or other suitable device such as a thrombolytic device or balloon may be inserted into the catheter. From the side branch 60, the guidewire 70, for example a 0.035" or a 0.018" guidewire, extends through the main lumen of the adapter 45 and into the lumen of catheter 20. In a particular embodiment, a selected treatment device may be inserted onto guidewire 70 and introduced into the vascular system of the patient through the catheter 20. The treatment device may be a percutaneous thrombolytic device, or a balloon device or some other device, useful to dislodge or break up blood clots 120. Other devices not employing the guidewire may be utilized.

A secondary catheter 65 may be inserted over the guidewire and advanced until the distal end of the secondary catheter 65 is positioned at the blood clot 120. A thrombolytic agent, such as a tissue plasminogen activator, may be delivered to the blood clot 120 through the secondary catheter 65 or systemically to promote dissolution of the clot 120 as an aid to withdrawal of the clot 120 through the catheter 20.

The proximal end of the catheter 20 is in fluid communication with the base 51 of a Y-shaped adapter 50. More specifically the adapter 45 is sealably connected to the base 51 of the Y-shaped adapter 50 thereby connecting the catheter with the Y-shaped adapter 51. First and second branches 52, 53 of the Y-shaped adapter 50 are in fluid communication with the filtration device 90 and a waste container 80, respectively. The Y-shaped adapter 50 includes a valve 55, such as a manually actuatable valve, capable of selecting either the first branch 52 or the second branch 53 so that the fluid flow of withdrawn blood can be selectably directed into the filter 90 or the waste container 80. As an alternative to manual actuation, valve 55 may be actuated by a motor 180.

The waste container 80 is further in gaseous communication with a waste suction source 190 which provides suction to the catheter 20. Application of suction withdraws blood clots 120 and any accompanying blood from the patient through the catheter 20 into the waste container 80. A valve or safety seal 102 may be utilized to prevent the flow of the blood from waste container 80 into waste suction source 190.

The distal end of the catheter 20 comprises a suitable tip for the removal of blood clots 120. Depending upon the particular application or procedure to be performed, for example, as shown in FIG. 2A, the tip of the catheter 20 may contain at least one hole in its side wall or optionally a plurality of side apertures through which blood may be withdrawn to prevent the blockage of suction by an inadvertent occlusion of the tip end.

As shown in FIG. 2B, the tip of the catheter 20 may be formed to extend at an angle from the longitudinal axis of catheter 20 to enable easier positioning of the tip in selected applications.

As shown in FIG. 2C, the tip of catheter 20 may be inwardly tapered toward the tip end so that the diameter of the catheter decreases towards the distal end of the catheter 20 to provide a tip end nozzle. The tapered tip may be preferable for use with smaller clots or where more precise positioning of the tip end is desired.

As shown in FIG. 2D, the catheter 20 may flare outwardly at the tip so that the catheter increases in diameter towards the tip end of the catheter 20. The outwardly flared end tip may be useful to encapture clot fragments that might otherwise flow by a narrower tip.

As shown in FIG. 2E, the distal end of the catheter 20 may be adapted to contain a hollow tubular insert 150 coaxially disposed within the distal end of the catheter 20. The tubular insert 150 is capable of slidable movement along the longitudinal direction of catheter 20 so that the tip of the insert may be moveable to extend outside of the catheter 20 beyond the distal end of catheter 20 or withdrawn back into the catheter. To effect movement of the tubular insert, a device may be attached to insert 150 as desired, such as a positioning catheter 154, which may be inserted through branch 60. Optionally, insert 150 may contain one or more holes 152 in the side wall of the insert 150. As the insert 150 extends beyond the distal end of catheter 20, a blood clot 120 may be drawn through the tip end while the side apertures function to prevent the blockage of suction.

As shown in FIG. 2F, a slidably extendable and retractable inner coaxial insert tube 151 may be provided wherein the tip end may expand in diameter as it extends beyond the distal end of catheter 20 to provide a flare tipped end. The flare tip of tube 151 may expand when deployed outside the catheter 20 and may collapse as the flare tip is retracted back into the catheter 20. The flare tip is useful to encompasses a greater diameter of the inside of a vessel to prevent clot fragments from by-passing the suction at the tip end.

As shown in FIG. 2G, the distal end of catheter 20 includes at least one strut 156 which traverses the distal end of the catheter 20. Optionally, a pair of criss-crossed struts 156 may be employed so that the struts 156 overlap or intersect at their midpoints. The struts 156 may bow outwardly beyond the distal end of catheter 20 to inhibit the occlusion of the distal end of the catheter 20. The struts may also function to facilitate the dislodgement and/or grinding of a clot to effect extraction. As shown in FIG. 2H, a plurality of struts 156 may be arranged to form a mesh.

A reinfuser 140, such as the Cell Saver type of device, is provided to reinfuse the filtered blood collected in the blood collection device 95 back into the patient. The reinfuser 140 may include a suitable blood injection assembly to deliver filtered blood back into the patient. The reinfuser 140 is in fluid communication with a suitable catheter, and reinfusion occurs through such catheter. The reinfuser 140 may communicate with catheter 20 via branch 60. In a particular arrangement, the blood collection device 95 is removable from the filtration device 90 so that the filtration device may be operably connected to the reinfuser 140 for reinfusion of the filtered blood into the patient. Alternatively, the blood collection device 95 may remain attached to the filtration device 90. In such an arrangement the reinfuser 140 must then be operably connected to the blood collection device 95 by appropriate tubing so that the reinfuser 140 reinfuses the filtered blood back into the patient while the blood collection device 95 remains attached to the filtration device 90.

Figure 3:
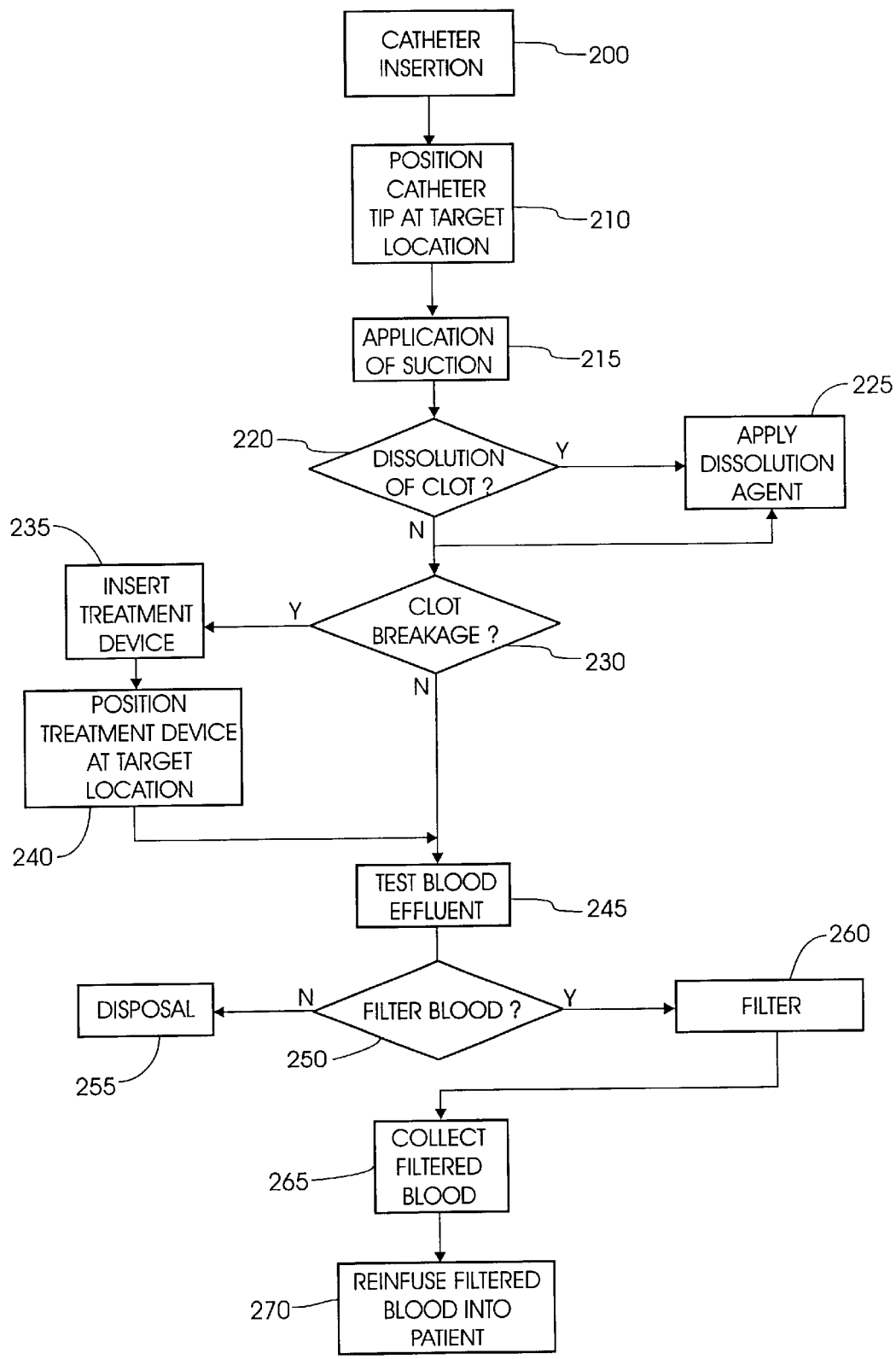
FIG. 3 is a flow chart showing a method for treating blood clots in accordance with the present invention.

Referring to FIG. 3, a catheter 20 is inserted, at step 200, percutaneously into a selected blood vessel of the vascular system of the patient and is advanced until the distal end of the catheter 20 is located, at step 210, at a blood clot 120 selected for removal. The catheter 20 may be introduced into the body through a vein or an artery, such as a femoral artery or vein or jugular vein so that the distal end of the catheter may be properly positioned at the target site for removal of the clot. The distal end of the catheter 20 may be located within the lumen of the blood vessel 130 or within the lumen of an organ, such as the heart. Further, the distal end of catheter 20 may be located within the lumen of a graft, such as an arterial bypass graft, a dialysis graft, or venous bypass graft.

Once the distal end of catheter 20 is positioned at the desired target location, suction is applied, at step 215, to the proximal end of catheter 20 by the suction source 110 via the blood filtration device 90 which is in fluid communication with the catheter 20. The suction is created by a suitable suction source 110, such as wall suction or a portable pump, which is in gaseous communication with the blood filtration device 90. The suction from the suction source 110 draws the blood clot 120 and any accompanying blood into the distal end of the catheter 20 thereby removing the clot 120 from the patient.

If dissolution of the clot is desired prior to removal at step 220, then a thrombolytic agent, such as tissue plasminogen activator, is delivered to clot 120, at step 225, through the catheter 20 or systemically to promote dissolution of the clot prior to its removal through the catheter 20. For this purpose, a secondary catheter 65 may be inserted over the guidewire 70 and advanced until the distal end of the secondary catheter 65 is at the blood clot 120. The thrombolytic agent, such as a tissue plasminogen activator, is delivered to the blood clot 120 through the secondary catheter 65 to promote at least partial dissolution of the clot as an aid to withdrawal of the clot through the catheter 20.

In a particular mode of operation where clot breakage or dislodgement is desired at step 230, a treatment device 160 is used to break up or dislodge the blood clot 120 prior to its removal. For example, a guidewire 70 may be inserted through branch 60 and advanced through the catheter 20 until the distal end of the guidewire 70 reaches the distal end of catheter 20. The treatment device 160 is positioned at the distal end of the guidewire 70 and is advanced into catheter 20, at step 235, until the treatment device 160 is in close proximity to the clot 120 at the target site at step 240. Alternatively, a treatment device may be used without a guidewire. The treatment device 160 may be a percutaneous thrombolytic device, a balloon device or some other suitable device useful to break up blood clots 120. The treatment device 160 is manipulated to effect the breakup of the blood clot 120.

The removed blood and blood clot 120 are transported through the catheter 20 and Y-shaped adapter 50 into the filtration device 90. In a first method of operation, the clarity of the blood is observed visually or otherwise tested at step 245, and any suctioned aliquot judged to contain too much clot to allow safe filtration, at step 250 is diverted into waste container 80 by actuation of valve 55 for disposal, at step 255. In an alternative method of operation, the clarity of the blood may be observed using a turbidity meter 170, and blood determined to be too turbid is diverted into waste container 80 using valve 55 which is actuated by a controller motor 180.

Blood having acceptable characteristics is transported through the Y-shaped adapter 50 into the filtration device 90 where the blood is filtered at step 260 to separate the clots 120 from the blood. The filtered blood is collected at step 265 and is then reinfused back into the patient.

In a first reinfusion method, the blood collection device 95 is removed from the filtration device 90 and operably connected to the reinfuser 140 for reinfusion of the filtered blood into the patient. In a second reinfusion method, the blood collection device 95 remains attached to the filtration device 90, and the reinfuser 140 is operably connected to the blood collection device 95.

The reinfuser 140 includes a delivery system for delivering the filtered blood-back into the patient. For this purpose, an IV needle and IV tubing may be provided. The tubing is connected at one end with the blood collection device and the IV needle is inserted into the vascular system of the patient. The reinfuser 140 draws the filtered blood from the blood collection device 95 and delivers it into the vascular system of the patient through the delivery device. In a preferred method, the delivery device of the reinfuser 140 includes catheter 20. The reinfuser 140 draws the filtered blood from the blood collection device 95 and delivers it to the patient through catheter 20. The reinfuser 140 may communicate with catheter 20 via branch 60. Optionally, the reinfusion step may be performed simultaneously with the suctioning step.

These and other advantages of the present invention will be apparent to those skilled in the art. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for removal of a clot in a blood vessel system of a patient using a thrombectomy treatment system, comprising the steps of:
   (a) introducing a catheter into a blood vessel system of a patient, the catheter having proximal and distal extremities;
   (b) advancing the catheter through a portion of the blood vessel system to position the distal extremity of the catheter at a desired location within the blood vessel system;
   (c) providing a filtration device in fluid communication with the proximal extremity of the catheter, the filtration device separable from the catheter;
   (d) applying suction from a suction source to the catheter near its proximal extremity to suction blood into the distal extremity of the catheter and through the filtration device without suctioning blood into the suction source;
   (e) diverting a portion of the suctioned blood into a waste container when the diverted blood does not meet a selected criteria of clarity;
   (f) filtering the suctioned blood with the filtration device to remove clots to provide a source of filtered blood; and
   (g) drawing the filtered blood from the source of filtered blood into a reinfuser and reinfusing the drawn filtered blood back into the patient.

2. A method for removal of a clot in a blood vessel system using a thrombectomy treatment system, comprising the steps of:
   (a) introducing a catheter into a blood vessel system of a patient, the catheter having proximal and distal extremities;
   (b) advancing the catheter through a portion of the blood vessel system to position the distal extremity of the catheter at a desired location within the blood vessel system;
   (c) applying suction from a suction source to the catheter near its proximal extremity to suction blood into the distal extremity of the catheter without suctioning blood into the suction source;
   (d) diverting a portion of the suctioned blood into a waste container;
   (e) filtering the suctioned blood to remove the clots; and reinfusing the filtered blood into the patient through the distal extremity of the catheter,
   wherein the non-diverted blood meets a selected criteria of clarity.

3. A thrombectomy treatment system comprising:
   (a) a catheter having proximal and distal extremities, the distal extremity for insertion into a blood vessel system of a patient;
   (b) a filtration device in fluid communication with the proximal extremity of the catheter for receiving suctioned blood from the catheter, the filtration device removable from the catheter and capable of filtering the blood to provide a source of filtered blood;
   (c) a suction source in gaseous communication with the filtration device for applying suction to the proximal extremity of the catheter, the suction source adapted to suction blood from the blood vessel system into the distal extremity of the catheter and into the filtration device without suctioning blood into the suction source;
   (d) a reinfuser removably connected in fluid communication with the filtration device for reinfusing the filtered blood back into the patient, the reinfuser having a drawing means for drawing blood from the source of filtered blood into the reinfuser, and
   (e) a turbidity meter for detecting the turbidity of the suctioned blood.

4. The system according to claim 3 comprising a valve in communication with the catheter and wherein the turbidity meter is operably connectable to a motor for causing actuation of the motor to move the valve to direct a flow of blood through the catheter.

5. The system according to claim 4 wherein the turbidity meter actuates the motor when the detected turbidity meets a predetermined value.

6. A thrombectomy treatment system comprising:
   (a) a catheter having proximal and distal extremities, the distal extremity for insertion into a blood vessel system of a patient;
   (b) a filtration device in fluid communication with the proximal extremity of the catheter for receiving suctioned blood from the catheter, the filtration device removable from the catheter and capable of filtering the blood to provide a source of filtered blood:
   (c) a suction source in gaseous communication with the filtration device for applying suction to the proximal extremity of the catheter, the suction source adapted to suction blood from the blood vessel system into the distal extremity of the catheter and into the filtration device without suctioning blood into the suction source; and
   (d) a reinfuser removably connected in fluid communication with the filtration device for reinfusing the filtered blood back into the patient, the reinfuser having a drawing means for drawing blood from the source of filtered blood into the reinfuser,
   wherein the filtration device includes a centrifuge.

* * * * *